(12) United States Patent
DeCheek et al.

(10) Patent No.: US 12,245,850 B2
(45) Date of Patent: *Mar. 11, 2025

(54) SYSTEM AND METHOD OF UTILIZING ECG SIGNAL FOR STATIC CATHETER TIP CONFIRMATION

(71) Applicant: Bard Access Systems, Inc., Salt Lake City, UT (US)

(72) Inventors: Anthony D. DeCheek, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,436

(22) Filed: Nov. 30, 2023

(65) Prior Publication Data

US 2024/0099604 A1     Mar. 28, 2024

Related U.S. Application Data

(63) Continuation of application No. 16/938,700, filed on Jul. 24, 2020, now Pat. No. 11,918,339.

(Continued)

(51) Int. Cl.
*A61B 5/06* (2006.01)
*A61B 5/00* (2006.01)
(Continued)

(52) U.S. Cl.
CPC ............... *A61B 5/061* (2013.01); *A61B 5/349* (2021.01); *A61B 5/6852* (2013.01);
(Continued)

(58) Field of Classification Search
CPC ....... A61B 5/061; A61B 5/349; A61B 5/6852; A61M 25/0068; A61M 25/0158;
(Continued)

(56) References Cited

U.S. PATENT DOCUMENTS 7,289,844 B2   10/2007   Misczynski et al.
9,463,301 B2   10/2016   Bukhman
(Continued)

FOREIGN PATENT DOCUMENTS

CN   101939738 A   1/2011
GB      2335747 A   9/1999
(Continued)

OTHER PUBLICATIONS

CN 201480011618.6 filed Aug. 31, 2015 Office Action dated Jun. 27, 2017.
(Continued)

*Primary Examiner* — Tasnim Mehjabin Ahmed
(74) *Attorney, Agent, or Firm* — Rutan & Tucker LLP

(57) ABSTRACT

Systems and methods for confirming the tip location of a catheter. The system can include an ivECG acquisition module for receiving ECG data from an implanted endovascular device and a notification module. The system can calculate PxI and distance parameters to determine the location of the tip of the implanted endovascular device relative to a predetermined location such as the cavoatrial junction. The system can use chaos theory and the concept of self-organized criticality (SOC) to determine parameters where P-waves are absent or atypical. The notification module can include one or more of an audio signal, a video signal, and a tactile signal. Also disclosed are systems and methods of establishing an electrical pathway within a previously positioned catheter, including saline columns and electrically conductive guidewires.

9 Claims, 10 Drawing Sheets

Related U.S. Application Data

(60) Provisional application No. 62/879,342, filed on Jul. 26, 2019.

(51) Int. Cl.
   *A61B 5/349* (2021.01)
   *A61M 25/00* (2006.01)
   *A61M 25/01* (2006.01)
   *A61M 25/09* (2006.01)

(52) U.S. Cl.
   CPC .... *A61M 25/0068* (2013.01); *A61M 25/0158* (2013.01); *A61M 25/09* (2013.01); *A61M 2025/0166* (2013.01); *A61M 2205/0233* (2013.01); *A61M 2205/581* (2013.01); *A61M 2205/582* (2013.01); *A61M 2205/583* (2013.01); *A61M 2210/125* (2013.01); *A61M 2230/04* (2013.01)

(58) Field of Classification Search
   CPC .............. A61M 25/09; A61M 25/0105; A61M 2025/0166; A61M 2205/0233; A61M 2205/581; A61M 2205/582; A61M 2205/583; A61M 2210/125; A61M 2230/04
   See application file for complete search history.

(56) References Cited

U.S. PATENT DOCUMENTS

| | | | |
|---|---|---|---|
| 9,999,750 B2 | 6/2018 | Bukhman | |
| 10,722,686 B2 | 7/2020 | Bukhman | |
| 11,918,339 B2* | 3/2024 | Decheek | A61B 5/065 |
| 2008/0234978 A1 | 9/2008 | Neumann et al. | |
| 2009/0005675 A1 | 1/2009 | Grunwald et al. | |
| 2009/0156926 A1 | 6/2009 | Messerly et al. | |
| 2009/0259124 A1 | 10/2009 | Rothenberg | |
| 2010/0036227 A1* | 2/2010 | Cox | A61B 5/283 600/509 |
| 2010/0261977 A1 | 10/2010 | Seely | |
| 2010/0317981 A1 | 12/2010 | Grunwald | |
| 2012/0143029 A1 | 6/2012 | Silverstein et al. | |
| 2013/0150740 A1 | 6/2013 | Narayan et al. | |
| 2014/0249505 A1* | 9/2014 | Bukhman | A61B 5/6852 604/528 |
| 2015/0216446 A1 | 8/2015 | Bukhman et al. | |
| 2016/0228019 A1 | 8/2016 | Grunwald et al. | |
| 2017/0021131 A1 | 1/2017 | Bukhman | |
| 2018/0296796 A1 | 10/2018 | Bukhman | |
| 2021/0023341 A1 | 1/2021 | Decheek et al. | |

FOREIGN PATENT DOCUMENTS

| | | |
|---|---|---|
| WO | 2009043144 A1 | 4/2009 |
| WO | 2010125116 A1 | 11/2010 |
| WO | 2012040487 A1 | 3/2012 |
| WO | 2014137841 A1 | 9/2014 |
| WO | 2021021663 A1 | 2/2021 |

OTHER PUBLICATIONS

CN 201480011618.6 filed Aug. 31, 2015 Office Action dated Mar. 29, 2018.
EP 14760648.7 filed Aug. 31, 2015 Supplementary Search Report dated Sep. 2, 2016.
EP 20846962.7 filed Feb. 9, 2022 Extended European Search Report dated Jul. 6, 2023.
PCT/US2014/019664 filed Feb. 28, 2014 International Search Report and Written Opinion dated May 30, 2014.
PCT/US2020/043580 filed Jul. 24, 2020 International Search Report and Written Opinion dated Oct. 19, 2020.
Pittiruti, et al. "The EKG Method for Positioning the Tip of PICCs: Results from Two Preliminary Studies." JAVA, vol. 13, No. 4, pp. 179-185, 2008.
U.S. Appl. No. 13/844,755, filed Mar. 15, 2013 Non-Final Office Action dated Feb. 25, 2015.
U.S. Appl. No. 13/844,755, filed Mar. 15, 2013 Notice of Allowance dated Aug. 28, 2015.
U.S. Appl. No. 14/772,069, filed Sep. 1, 2015 Non-Final Office Action dated Apr. 27, 2016.
U.S. Appl. No. 15/286,418, filed Oct. 5, 2016 Advisory Action dated Dec. 1, 2017.
U.S. Appl. No. 15/286,418, filed Oct. 5, 2016 Final Office Action dated Oct. 12, 2017.
U.S. Appl. No. 15/286,418, filed Oct. 5, 2016 Non-Final Office Action dated Jun. 23, 2017.
U.S. Appl. No. 15/286,418, filed Oct. 5, 2016 Notice of Allowance dated Jan. 17, 2018.
U.S. Appl. No. 16/011,409, filed Jun. 18, 2018 Final Office Actino dated Apr. 23, 2020.
U.S. Appl. No. 16/011,409, filed Jun. 18, 2018 Non-Final Office Actino dated Jan. 29, 2020.
U.S. Appl. No. 16/938,700, filed Jul. 24, 2020 Non-Final Office Action dated Jun. 22, 2023.
U.S. Appl. No. 16/938,700, filed Jul. 24, 2020 Notice of Allowance dated Oct. 17, 2023.
U.S. Appl. No. 16/938,700, filed Jul. 24, 2020 Restriction Requirement dated Mar. 2, 2023.

* cited by examiner

SYSTEM AND METHOD OF UTILIZING ECG SIGNAL FOR STATIC CATHETER TIP CONFIRMATION

PRIORITY

This application is a continuation of U.S. patent application Ser. No. 16/938,700, filed Jul. 24, 2020, now U.S. Pat. No. 11,918,339, which claims the benefit of priority to U.S. Provisional Application No. 62/879,342, filed Jul. 26, 2019, each of which is incorporated by reference in its entirety into this application.

SUMMARY

The placement of most endovascular devices can be crucial to the success of the procedure and overall health of the patient. These endovascular devices can include various central venous catheters ("CVC"), peripherally inserted central catheters ("PICC"), ports, hemodialysis catheters, tunneled catheters, and the like. Various systems and methods can be employed to correctly place a distal end of the endovascular device within the body of a patient. Exemplary systems can include the Sherlock 3CG® Tip Confirmation System by Bard Access Systems, or similar endovascular device placement systems. Such exemplary systems and methods can track the location and confirm the placement of catheter as it moves through the vasculature, termed "dynamic" catheter placement.

Some methods of ECG based guidance employ morphological and/or spectral analysis of ECG waveforms, specifically P-waves, to track and confirm the location, for example as disclosed in U.S. Pat. No. 9,339,206, which is incorporated by reference in its entirety into this application. In addition, assessment of the location of the catheter tip can be performed by analyzing ECG data point to point variability. This method does not rely on P-wave morphology and so accommodates atypical sinus rhythm, for example as disclosed in US 2018/0296796, which is incorporated by reference in its entirety into this application.

Briefly summarized, embodiments disclosed herein are directed to systems and methods of establishing an electrical pathway in a static endovascular device, which has previously been placed within a patient, to confirm that a distal portion thereof is correctly positioned. The system can utilize ECG wave morphology to confirm the position of the distal portion in patients. Further, the system can utilize point to point variability of ECG data to compensate for atypical sinus rhythm or where the P-wave is absent. Accordingly, where the distal portion of a static, indwelling endovascular device has been dislodged, corrective action can be taken prior to any treatment.

In an aspect of the invention, a tip confirmation system for confirming a location of a tip of a static endovascular device, is disclosed. The system comprises an ivECG acquisition module, a multiscale complexity analysis module, an audio/video/tactile notification module, an electrical pathway extending from a distal tip of the static endovascular device to a proximal end thereof, and an adaptor designed to couple the electrical pathway with the ivECG acquisition module, wherein the multiscale complexity analysis module uses ivECG signals, provided by the ivECG acquisition module and the electrical pathway, to provide a PxI (proximity index), the audio/video/tactile notification module indicating a location of the distal tip of the static endovascular device relative to a predetermined target location.

In some embodiments, the electrical pathway includes an embedded electrode extending from a proximal hub to a distal tip of the static endovascular device. The electrical pathway includes an electrically conductive device disposed within a lumen of the static endovascular device, and extending from a proximal hub to a distal tip thereof. The electrically conductive device includes one of a stylet, a guidewire, and a trocar. The electrical pathway includes a saline column extending from a proximal hub to a distal tip of the static endovascular device. The static endovascular device includes one of a central venous catheters (CVC), a peripherally inserted central catheter (PICC), a port, a hemodialysis catheter, a tunneled catheter, and a guiding catheter.

Also disclosed is a method of confirming the location of a tip of an indwelling catheter, the method comprising: providing tip confirmation system including an ivECG acquisition module, a multiscale complexity analysis module, and audio/video/tactile notification module, establishing an electrical pathway between a proximal end and a distal end of the indwelling catheter, the electrical pathway providing ECG data from a location of the distal tip of the indwelling catheter to a proximal end thereof, coupling the ivECG acquisition module with a proximal end of the electrical pathway, calculating a proximity index (PxI) function from the ECG data, and indicating a location of a distal tip of the indwelling catheter relative to a target location using the PxI function.

In some embodiments, establishing an electrical pathway includes flushing the indwelling catheter with an electroconductive solution to establish a saline column between a proximal end and a distal end thereof. Establishing an electrical pathway includes disposing an electrically conductive guidewire within a lumen of the static catheter, the guidewire extending from a distal tip to a proximal end of the static catheter. The target location is a cavoatrial junction.

Also disclosed is a method of utilizing an ECG signal for reconfirming the tip location of a static CVC catheter, the method comprising: establishing an electrical pathway between an proximal end and a distal end of the static CVC catheter, the distal end disposed within a vasculature of a patient and the proximal end disposed external to the patient, receiving ivECG signal data from a distal tip of the static CVC catheter, deriving a PxI (proximity index) parameter, wherein the PxI parameter is a chaos theory complexity parameter associated with variability of the ivECG signal data, providing an output indicative of proximity of the distal tip of the static CVC catheter to the cavoatrial junction.

In some embodiments, establishing an electrical pathway includes flushing the static CVC catheter with a saline solution to establish a saline column and electrically coupling the saline column with an ivECG acquisition module. Establishing an electrical pathway includes extending an electrically conductive guidewire through a lumen of the static CVC catheter so that a distal tip of the guidewire extends to a distal tip of the CVC catheter and coupling a proximal end of the guidewire with an ivECG acquisition module.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

The terms "upper," "lower," "top," "bottom," "underside," "upperside" and the like, which also are used to describe the present system, are used in reference to the illustrated orientation of the embodiment. The terms "left" and "right" are used consistently throughout the disclosure and are used to describe structures from the perspective of the user or clinician using the device. As used herein a "dynamic" catheter is a device that is being advanced through the vasculature of a patient, and a "static" catheter is a device that device that has already been placed in the vasculature of a patient.

Catheter Placement Confirmation

Embodiments described herein are generally directed to a system and method for tip confirmation of a static endovascular device, such as a CVC catheter in the superior vena cava ("SVC"). While this system and method may be discussed in terms of confirming the location of a CVC tip in the SVC, the principles used in the system and method may be applied to a broader range of systems, methods, and devices. For example, the principles may be applied to different types of catheters or devices (e.g., CVC, PICC, ports, hemodialysis catheters, pacemaker leads, and the like) disposed in the SVC or in selected veins, arteries, or parts of the body other than, or in addition to, the SVC to achieve particular results.

As discussed in more detail below, the system and method include establishing an electrical pathway between a proximal end and a distal end of a static, indwelling, catheter. Evaluating the complexity of changes of an ivECG signal to calculate the position of an endovascular device, e.g., to calculate the distance from the tip of a CVC to the cavoatrial junction. Comparing the ivECG signal with historical data, predetermined reference points, combinations thereof, or the like, to re-confirm the correct positioning of the tip or determine if the tip requires repositioning. The method is based on chaos theory and the concept of self-organized criticality (SOC).

Figure 1:
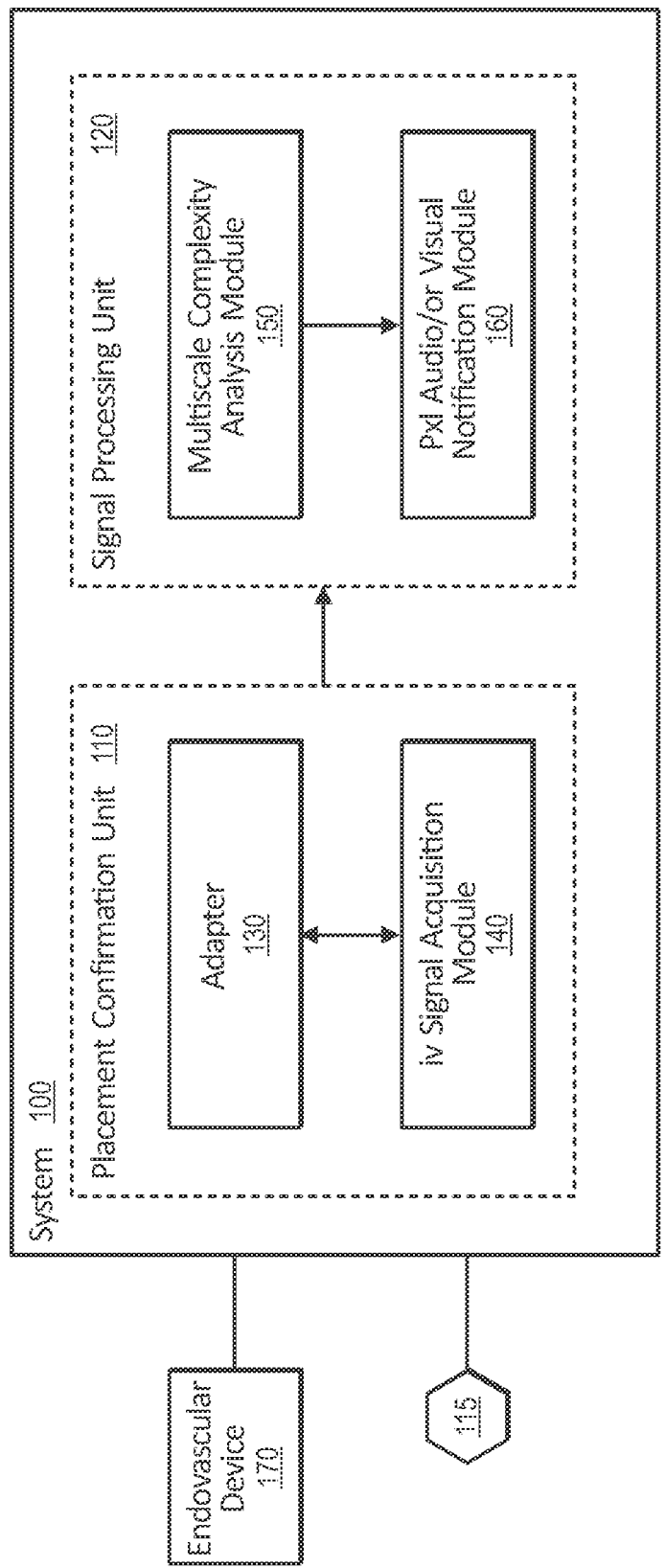
FIG. 1 shows a block diagram depicting various elements of a system for tip confirmation of an endovascular device, according embodiments described herein.

FIG. 1 shows a simplified block diagram of an endovascular placement confirmation system ("system") 100. The system 100 includes placement confirmation unit 110 and signal processing unit 120. Placement confirmation unit 110 includes adaptor 130 and ivECG signal acquisition module 140. The adaptor 130 may include any components necessary to provide an electrical pathway between the endovascular device, e.g. endovascular device 170, and the ivECG signal acquisition module 140. The ivECG signal acquisition module 140 may be a combination of hardware and software used to acquire a signal, e.g., an ivECG signal.

The system 100 can be attached through an adaptor 130 to a large variety of commercially available and custom designed vascular access devices 170. Examples of such devices are central venous catheters (CVC), peripherally inserted central catheters (PICC), implantable ports, tunneled catheters, hemodialysis catheters, guiding catheters for pacemaker leads, guidewires used for coronary and other vascular interventions, guiding catheters for coronary and other vascular interventions, stylets, syringe needles, and the like. If the vascular access device is a stylet, a guidewire, or a syringe needle, its material must be sufficiently electrically conductive, e.g., stainless steel or nitinol. In such a case the hook or the alligator clip adaptor according to one embodiment should be used. If the vascular access device is a catheter, then a saline column can be used to establish a conductive path through one of the catheter's lumens. In such a case, a syringe-catheter adaptor according to one embodiment can be used. Further details of embodiments of adaptors and associated endovascular devices can be found in U.S. Pat. No. 10,271,762, which is incorporated by reference in its entirety in this application.

Figure 2:
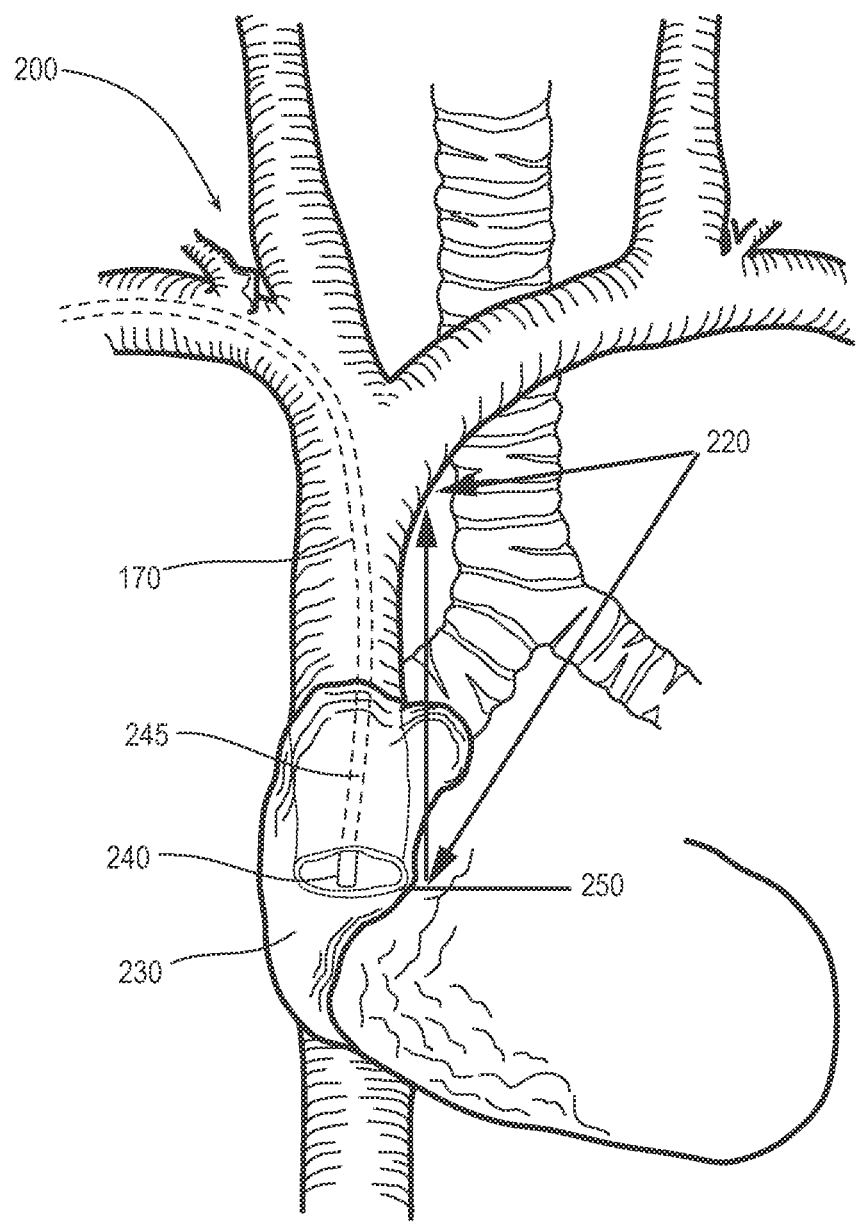
FIG. 2 shows an endovascular device disposed within the vasculature of a patient for use with the system of FIG. 1.
Figure 3:
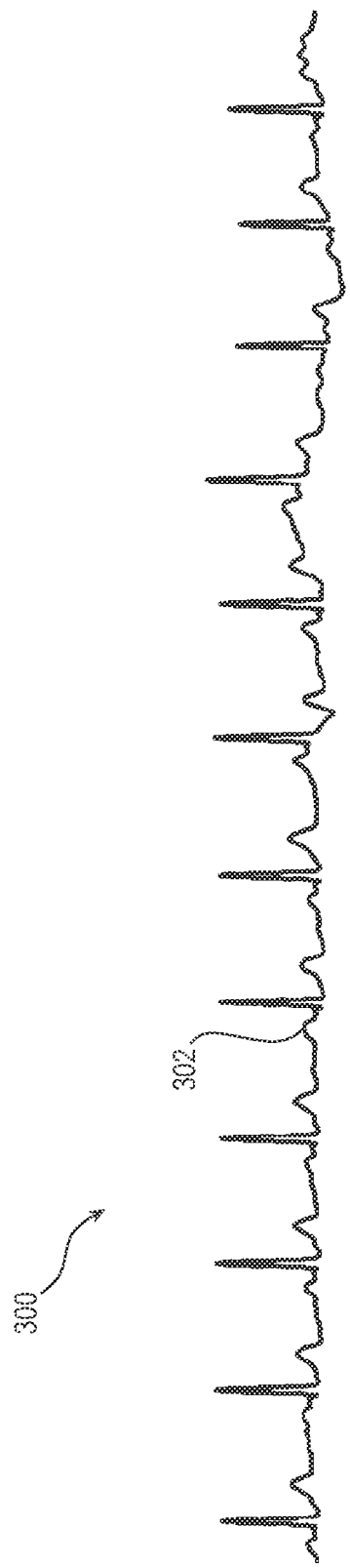
FIG. 3 shows a plotted ivECG time series recorded by an ivECG device.

FIG. 2 shows a drawing of a heart 200 and surrounding vasculature. The endovascular device 170 is shown placed in SVC 220 in an optimal position at the border 250 between the atrium 230 and SVC 220, i.e., the cavoatrial junction. In an embodiment, the endovascular device 170 includes an electrically conductive pathway 245 extending from a distal tip 240 of the endovascular device to a hub located at a proximal end (not shown) of the endovascular device 170. The ivECG acquisition module 140 can then be coupled with a proximal end of the electrically conductive pathway 245 to retrieve ivECG signals detected at a distal tip 240. FIG. 3 shows a representative ivECG waveform 300 acquired by the endovascular device 170, as well as a P wave 302.

The ivECG signal acquisition module 140 receives electrical signals from the adaptor 130 and from one or more other electrodes placed on the patient's skin 115. Alternatively, more than one adaptor 130 can be used at the same time to connect to more than one endovascular device in order to provide different electrical signals to the ivECG signal acquisition module 140. The use of skin electrodes is optional in certain device configurations. The ivECG signal acquisition module 140 processes the electrical signals and transmits them to a signal processing unit 120 for further processing and other functions. In one embodiment the ivECG signal acquisition module 140 and the signal processing unit 120 can be provided as separate units. In an embodiment the ivECG signal acquisition module 140 and the signal processing unit 120 can be integrated in the same unit.

The signal processing unit 120 includes multiscale complexity analysis module 150 and Proximity Index ("PxI") audio and/or visual notification module 160. In one embodiment the notification module 160 includes a tactile feature that provides a sensation, such as haptic feedback, which can be included along with the notification module 160, or could be a stand-alone feature to indicate PxI. The signal processing unit 120 utilizes the signal, e.g., the ivECG signal, acquired by the acquisition module 140 for confirmation of the endovascular device position. Multiscale complexity analysis module 150 may include software programmed for signal data processing. For example, multiscale complexity analysis module 150 may be programmed for processing ivECG signal data acquired from the acquisition module 140 to calculate a PxI parameter and/or the distance between the endovascular device and a predetermined location, such as the cavoatrial junction. Further details on the methods and algorithms used to calculate the PxI parameter and/or the distances can be found in U.S. Pat. Nos. 9,999,750; 9,463,301; 9,220,432, and U.S. Pub. No. 2018/0296796, each of which is incorporated by reference in its entirety into this application.

For example, as disclosed in the aforementioned patents and publication, Multiscale Complexity Analysis (MSCA) of dynamics of ivECG data using a Complementary Probability Cumulative Distribution Function, also called Tail Distribution, adapted for the analysis of dynamics of ivECG data. Tail Distribution is defined by the following equation (where P is the probability that the random variable X takes on a value more than x):

$$\overline{F}(x) = P(X > x)$$

The endovascular device 170 with the electrically conductive pathway 245 outputs the time series of ivECG data as a set of measured voltage amplitudes, $\{v_1, v_2, v_3, \ldots v_i, v_{i+1}, \ldots v_n\}$. ivECG time series is transformed to the time series of differences of successive points $\{d_1, d_2, d_3, \ldots d_i, d_{i+1}, \ldots d_{1-1}\}$ where $d_i$ is the absolute difference, $|v_{i+1} - v_i|$ between successive points $v_{i+1}$ and $v_i$.

$P_i$ is the Probability in percentages that the absolute difference between the measured values of Successive Points is more than x.

$$P_i = P(d_i > x), \text{ where } d_i \text{ is } |v_{i+1} - v_i|$$

$P_i$ value at value x=a is the measurement of complexity at scale a. Plotting $P_i$ values with x varying from 0 to maximum of $d_i$ provides a graph of multiscale complexity of ivECG dynamics. $P_i$ represents the tail distribution.

Figure 4:
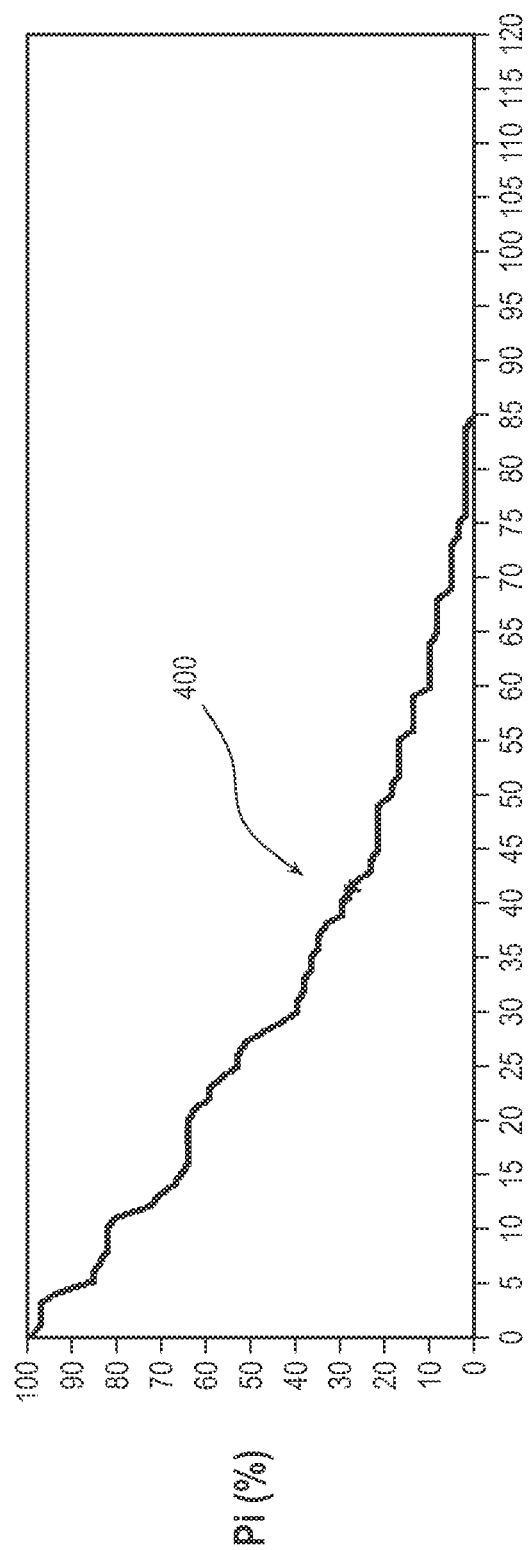
FIG. 4 illustrates a representative tail distribution graph for an ivECG time series.

FIG. 4 shows a graphical representation of the tail distribution 400 for the ivECG signal/time series 300 in FIG. 3. Whereas, FIG. 4 depicts a tail distribution curve 510 of another ivECG signal as measured at the entrance of the SVC, and a tail distribution curve 520 of ivECG signal as measured in close proximity to the cavoatrial junction. The tail distributions of various ivECG signals, e.g., as shown in FIGS. 3 and 4, may be calculated using the above equations. Referring again to FIG. 1, algorithms may be programmed into multiscale complexity analysis module 150 to perform these functions and calculate tail distributions for signals acquired by acquisition module 140. Proximity Index (PxI) is calculated as a density of Tail Distribution Function (TDF) which is defined as $$TDF[a \le x \le b] \int_a^b f(x)dx$$

For discrete values (e.g., discrete values of ivECG signal data) the equation becomes as follows (where max is an empirical cut off value representing maximal difference between the largest and smallest two consecutive values of $v_i$ and $v_{i+1}$):

$$TDF[0 \le x \le \max] = \sum_{i=0}^{max} p_i x_i$$

Figure 5:
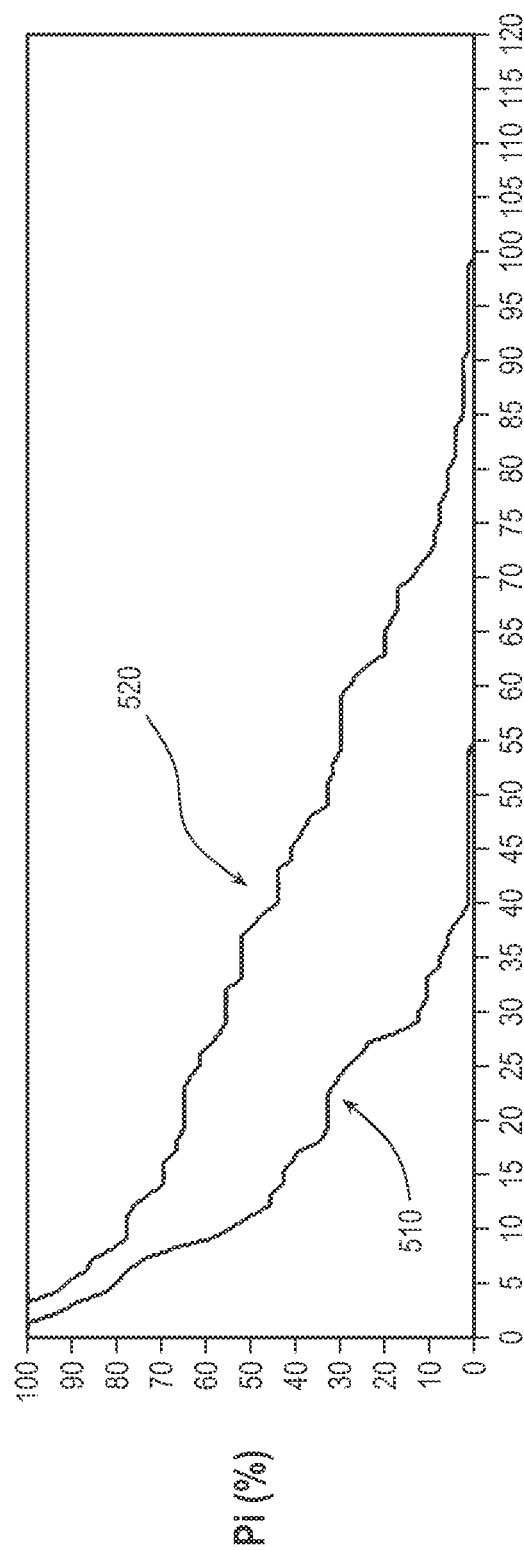
FIG. 5 shows tail distribution graphs of an ivECG time series at the entrance of the SVC and in close proximity to the cavoatrial junction.
Figure 6:
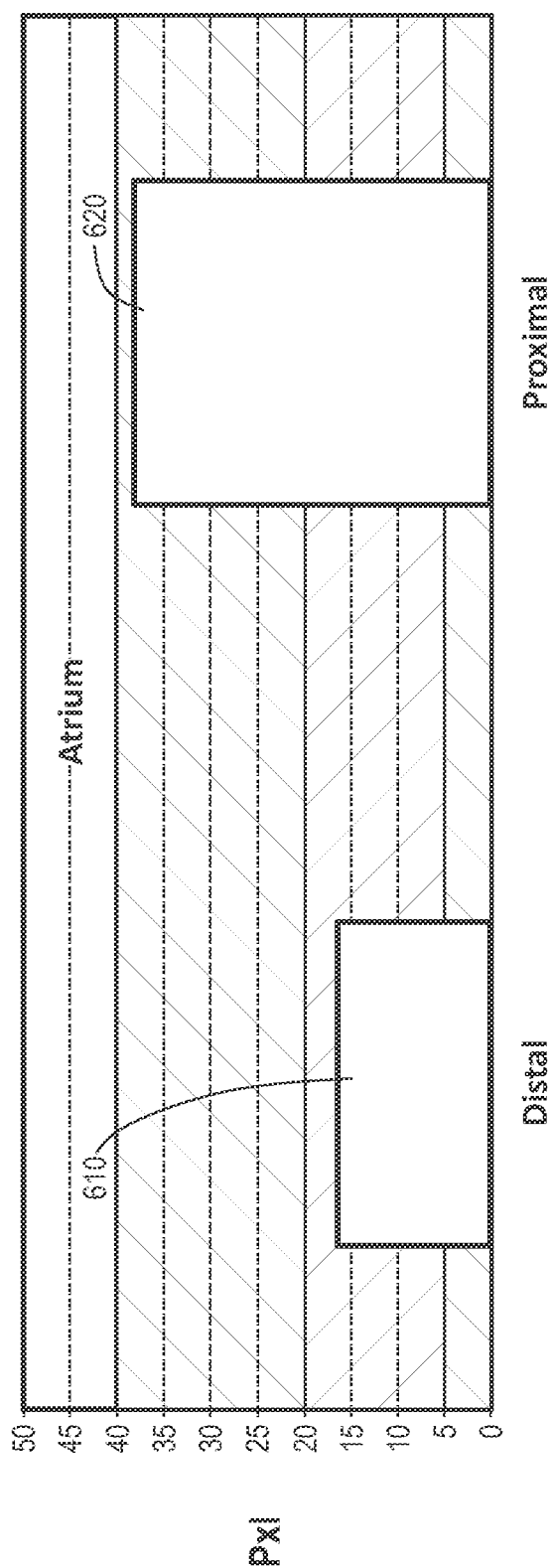
FIG. 6 illustrates the Proximity Index (PxI) or the density of the tail distribution shown in FIG. 5.
Figure 7:
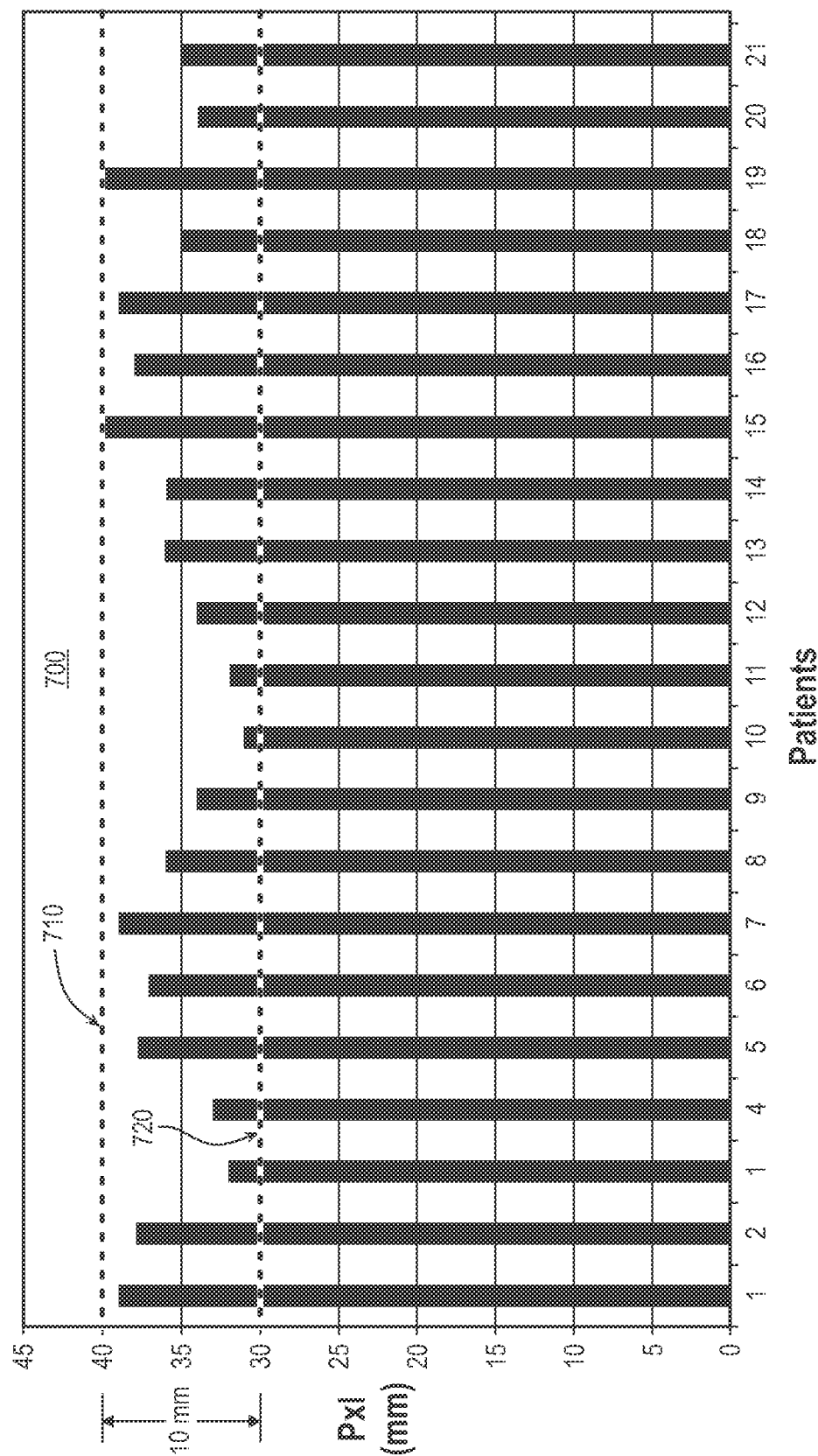
FIG. 7 shows PxI values for a group of 21 patients.

FIG. 6 illustrates graphical representations of PxI values for the ivECG signals used to form the tail distributions of FIG. 5, including PxI value 610 of the ivECG signal measured at the entrance of the SVC, and PxI value 620 of the ivECG signal measured in close proximity to the cavoatrial junction. FIG. 7 shows a graphical representation 700 of actual PxI values for the tip confirmation of 21 patients. All placements of the CVC tip are within 10 mm from the cavoatrial junction as represented by the dotted line 710 at the nominal value 40 of PxI. In other words, the PxI values for each patient are above the proximity threshold shown by dotted line 720. When the PxI values cross the proximity threshold 720 at the nominal value of 30 PxI, this indicates that the tip of the CVC catheter is within the 10 mm of the cavoatrial junction. If the PxI values crossed threshold 710, this would indicate that the tip of the CVC catheter has passed the cavoatrial junction and entered the atrium. Using this method of analysis, a clinician can confirm that the tip of the endovascular device 170 is correctly placed. PxI values of various ivECG signals, e.g., as shown in FIGS. 6 and 7, may be calculated using the above equations. Referring again to FIG. 1, algorithms may be programmed into multiscale complexity analysis module 150 to perform these functions and calculate PxI and correlate PxI to distance between the endovascular device and the cavoatrial junction, e.g., the distance between the tip of a CVC and the cavoatrial junction.

Figure 8:
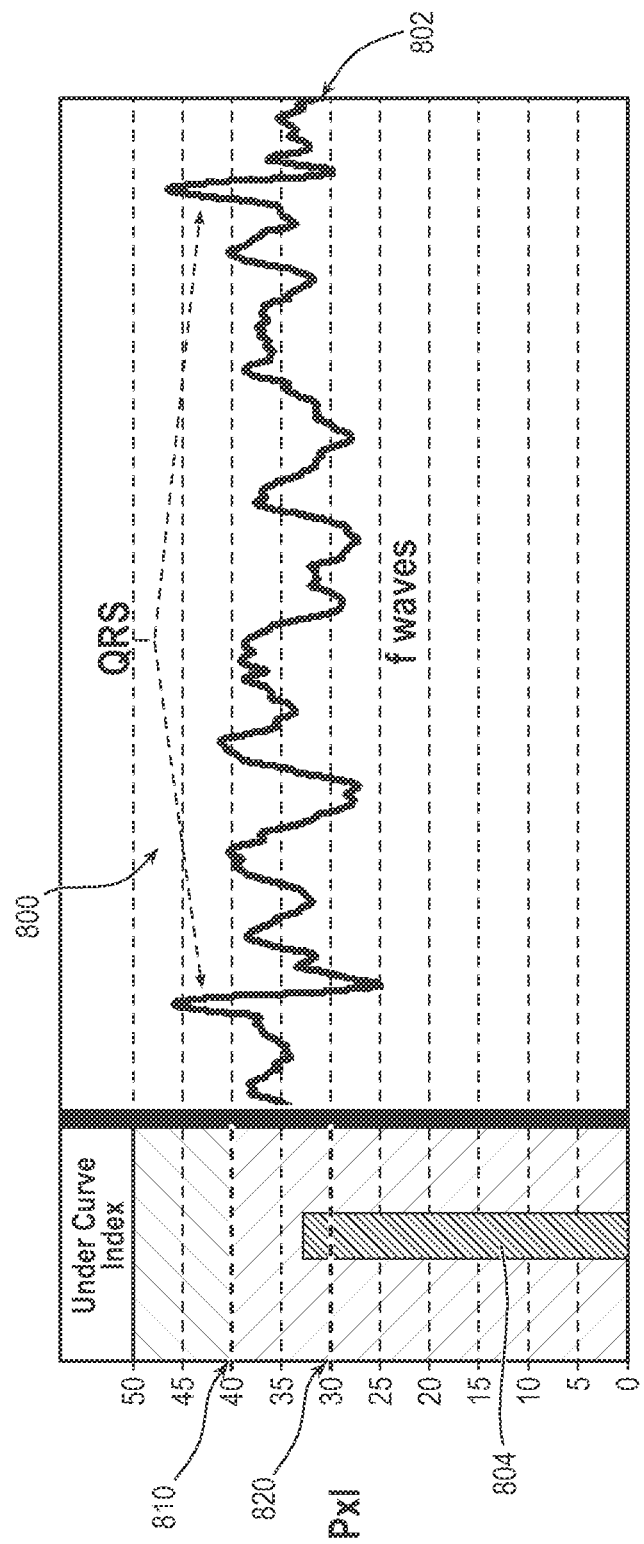
FIG. 8 shows a PxI value for a patient with atrial fibrillation and a corresponding ivECG time series.

FIG. 8 illustrates the CVC tip confirmation 800 for a patient with atrial fibrillation. The ivECG signal data 802 for the patient is shown on the right, and the PxI value 804 calculated from this signal data is shown on the left. A proximity threshold 820 signaling the point at which the tip is within 10 mm of the cavoatrial junction and a threshold 810 signaling the point at which the tip is at the cavoatrial junction are also shown. As shown in the ivECG signal data 802 of FIG. 8, P wave analysis is impossible during atrial fibrillation, e.g., because P waves are absent or distorted. This can be seen by comparing the signal data 802 of FIG. 8 with the signal data 300 and P wave 302 of FIG. 3. Accordingly, methods using assessment of morphological changes of P waves of ivECG are not applicable for patients with atrial fibrillation. In contrast, the above method of confirming the location of an endovascular device placed at the cavoatrial junction using multiscale complexity analysis and identifying PxI, and then comparing it with a proximity threshold is unaffected by atrial fibrillation. Accordingly, the disclosed method allows for accurate confirmation of the endovascular device even in cases of atrial fibrillation or other distortion of the waveform.

The audio/visual/tactile notification module 160, may include hardware and software that signals an associated device (e.g., a monitor, computer, audio device, and/or other display) to provide the user with an audio, visual, and/or tactile indication/notification of PxI and/or the proximity of the endovascular device to the predetermined location. The audio, visual, and/or tactile notification may take a variety of forms, including as a graphical or numerical display of PxI, a graphical or numerical display of distance between the endovascular device and the cavoatrial junction, a graphical representation of the endovascular device moving relative to a graphical representation of the heart and/or SVC (e.g., an image of a CVC tip may be shown in an image of the SVC at the cavoatrial junction), a sound (e.g., a beep) that changes frequency depending on the location of the endovascular device relative to the desired location, display colors may change depending on the location of the endovascular device (e.g., a red color may be displayed if the tip is incorrectly positioned), a vibration of one or more of the components of the system (e.g., haptic feedback), a change in temperature of one or more of the components of the system, etc., and combinations thereof.

It will be appreciated that various components, or sub-components, of the system 100, e.g. placement confirmation unit 110, signal processing unit 120, adaptor 130, endovascular device 170, skin electrodes, and the like, can provided as separate units that are coupled together using wired or wireless communication or can be combined together as a single unit, or combinations thereof. In an embodiment, the connection between the ivECG signal acquisition module 140 and the signal processing unit 120 can be hardwired, and in another embodiment the connection can be wireless, e.g., using Bluetooth, WiFi, etc. In one embodiment the signal processing unit 120 can be a laptop computer, netbook, handheld device, tablet, smartphone, or the like.

Optionally, the signal processing unit 120 may be embedded in a placement confirmation unit 110, for example, if the placement unit 110 has a built-in digital signal processing unit (DSP). Alternatively, the signal processing unit 120 may utilize a separate DSP connected to placement unit 110. The signal processing unit 120 and/or DSP may be implemented using integrated circuits, microprocessors, field-programmable gate arrays (FPGAs), digital signal controllers, stream processors, software, and/or other components.

Figure 9:
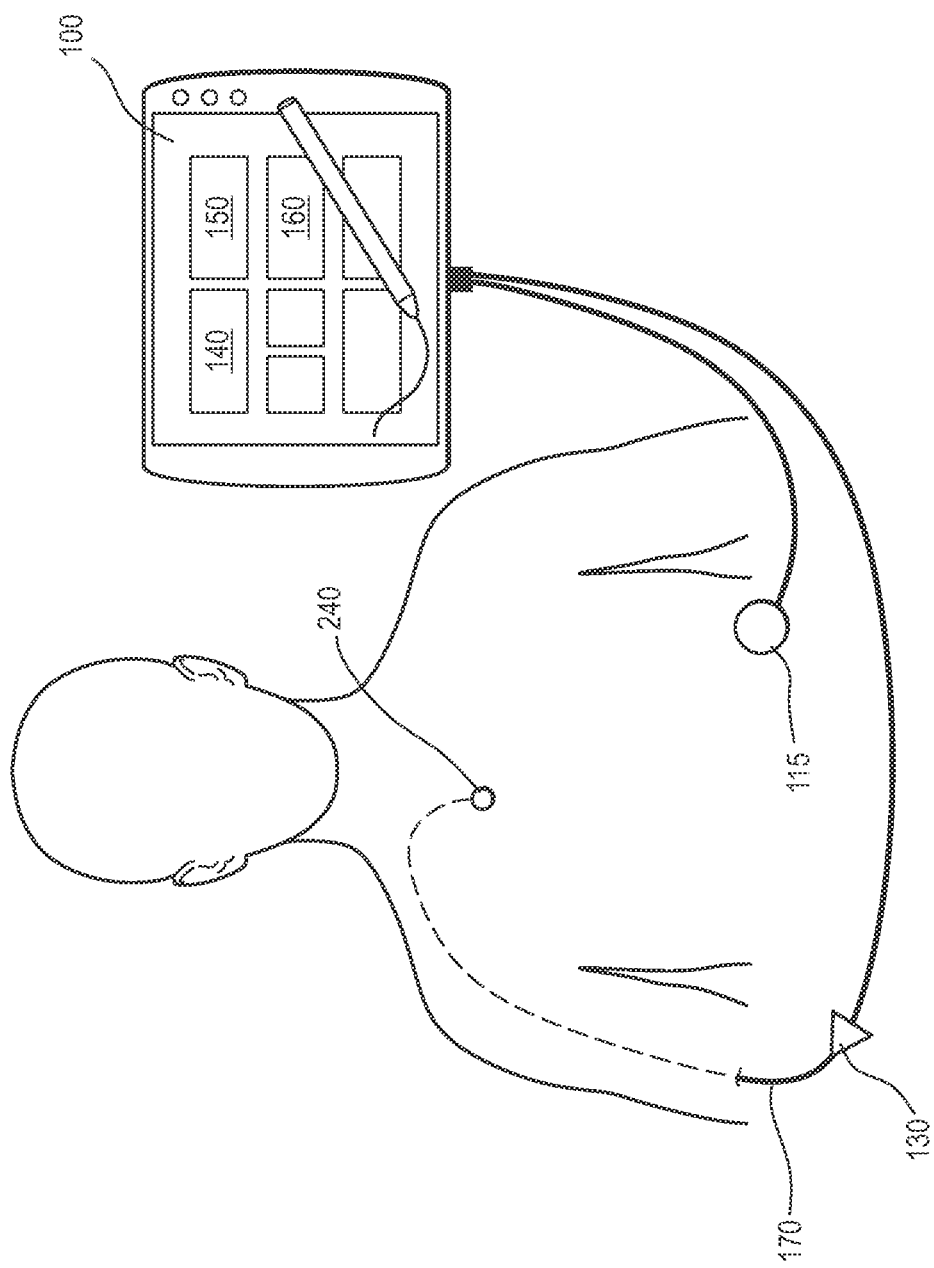
FIG. 9 shows an exemplary environment of use for the system of FIG. 1.

FIG. 9 shows an exemplary environment of use for the system 100. In an embodiment, the ivECG signal acquisition module 140, multiscale complexity analysis module 150, and the audio/visual/tactile notification module 160 can be disposed in a single handheld unit such as a tablet computer or the like. The system can then be communicatively coupled with an adaptor 130 and optionally one or more other electrodes placed on the patient's skin 115. As used herein communicatively coupled can include wired or wireless communication, or combinations thereof. The adaptor 130 can then be coupled with an electrical pathway extending through the endovascular device 170 to a distal tip 240 thereof.

Figure 10:
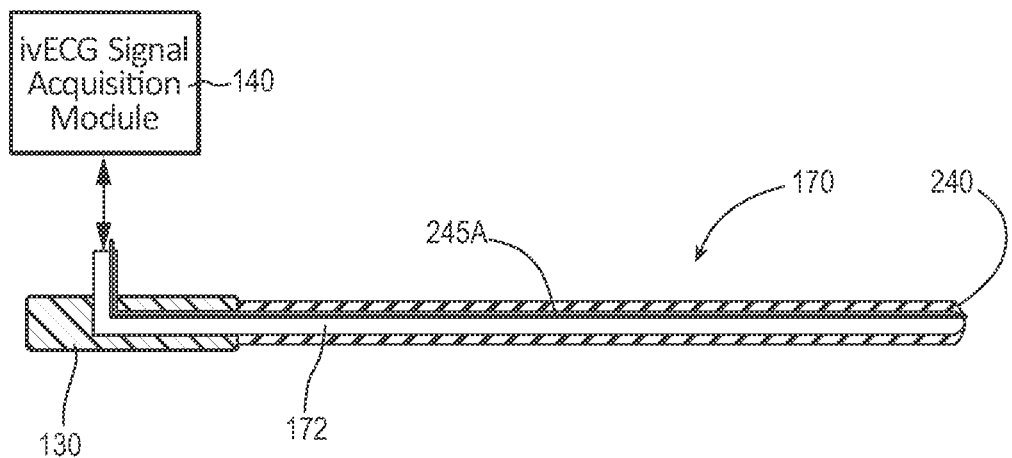
FIG. 10 shows one embodiment of an endovascular device for use with the system of FIGS. 1 and 9.
Figure 11:
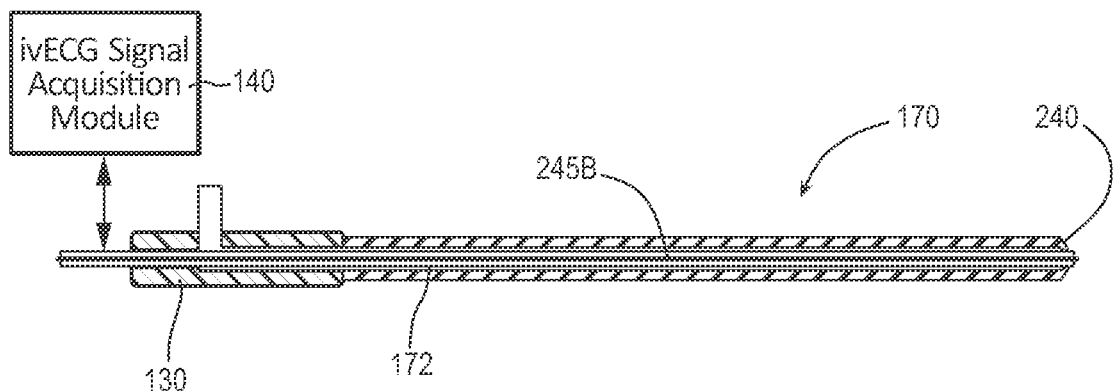
FIG. 11 shows another embodiment of an endovascular device for use with the system of FIGS. 1 and 9.
Figure 12:
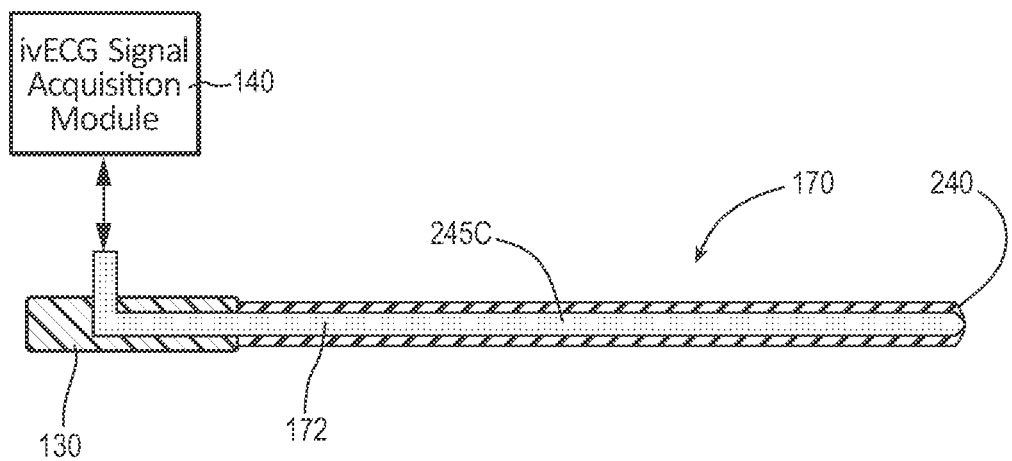
FIG. 12 shows another embodiment of an endovascular device for use with the system of FIGS. 1 and 9.

FIGS. 10-12 show various embodiments of the endovascular device 170 including an electrically conductive pathway 245. Further details of which can be found in U.S. Pat. No. 10,271,762, which is incorporated by reference in its entirety into this application. As shown in FIG. 10, in an embodiment, the endovascular device 170 includes an electrode 245A embedded in a wall of the endovascular device 170. The electrode 245A extends from a distal tip 240 to a hub or adaptor 130 at a proximal end. The distal tip of the electrode 245A can be exposed to detect any electrical impulses received at the distal tip 240 of the endovascular device 170. In an embodiment, a distal tip of the electrode 245A can extend distally of the distal tip 240 of the endovascular device 170. The electrode 245A can be co-extruded with the endovascular device 170 to allow the lumen 172 of the endovascular device 170 to remain unobstructed. In an embodiment the electrode 245A can be disposed within a secondary lumen disposed in a wall of the endovascular device 170.

As shown in FIG. 11, in an embodiment, the endovascular device 170 includes an electrically conductive guidewire 245B disposed therein. It will be appreciated that similar devices to the guidewire 245B are also contemplated. These devices can also be disposed within a lumen of the endovascular device 170 and extend to, or beyond, a distal tip 240 of the endovascular device 170. Such devices include stylets, guidewires, trocars, or the like formed of electrically conductive material such as stainless steel, nitinol, or the like. The adaptor 130 can allow the introduction of the guidewire 245B into a lumen of the endovascular device 170 and advanced until a distal tip of the guidewire 245B extends to, or beyond, a distal tip of the endovascular device 170. A proximal end of the guidewire 245B can be coupled with the ivECG acquisition module 140. Optionally, the guidewire 245B can include an electrically insulating coating that covers substantially the entire length of the guidewire 245B while allowing a proximal portion and a distal portion of the guidewire 245B to remain exposed, allowing electrical connections to be formed.

As shown in FIG. 12, in an embodiment, the electrically conductive pathway 245 includes a saline column 245C. An adaptor 130 can be coupled with the endovascular device 170 and include a T-adaptor to allow the lumen 172 to be flushed with a saline solution or similar electrically conductive solution. The adaptor 130 further includes electrodes to electrically couple a proximal end of the saline column with the ivECG acquisition module 140. Electrical signals detected at a distal tip 240 of the endovascular device 170 can be transferred to the ivECG acquisition module 140 by way of the saline column and adaptor 130. In this way, the electrical signal at the tip of the catheter may be measured through the saline solution. In an embodiment, the adaptor 130 may be used with infusion pumps, as well as other types of power injections.

Advantageously, systems and methods, disclosed herein establish an electrical pathway between proximal and distal ends a static, indwelling catheter that has already been placed within a patient. The proximal end of the catheter can then be coupled with an ivECG acquisition module 140 to determine a location of a distal tip of the endovascular device. The system 100 can then confirm the tip is correctly position, for example, to within +/−2 cm of the sinoatrial (SA) node. Alternatively, if the tip has become dislodged corrective action can be taken prior to any treatment.

As noted above, in one embodiment, the system may optionally include one or more external electrodes to provide an external ECG in combination with the ivECG in order to determine the location of the distal tip of the endovascular device. The one or more external electrodes or leads 115 are placed on the skin of the patient, and connected to the system. In one embodiment, the connection to the system is through an additional module, e.g., an ECG module. Examples of electrodes or leads, ECG modules, and the incorporation thereof into location systems are shown and described, for example, in U.S. Pat. No. 8,849,382, which is incorporated by reference in its entirety into this application.

Method for Confirming the Tip Location of an Endovascular Device

An exemplary method of confirming the position of a tip of a static endovascular device, such as a central venous catheter (CVC) is presented below.

Determine the length of the implanted CVC according to historical data, patient anatomy, or combinations thereof. Insert a conductive guidewire (or stylet) into a proximal end of the CVC by way of adaptor 130. If the length of the CVC is predetermined, advance the guidewire until a distal tip of the guidewire is flush aligned with the catheter tip. If the length of the CVC is not known, connect a proximal end of the guidewire to the ivECG signal acquisition module 140 and advance the guidewire until an increase in ECG signal is detected. The guide wire disposed within the CVC will be shielded from any ECG signals until a distal tip of the guidewire extends beyond a distal tip of the CVC, at which point the ECG signal will increase. Retract the guidewire until the ECG signal drops and the distal tips of the guidewire and CVC are flush aligned. Connect the adapter 130 to ivECG signal acquisition module 140.

The Multiscale Complexity Analysis Module 150 receives ECG signals from the ivECG signal acquisition module 140 and calculates a PxI parameter. The PxI audio/visual/tactile notification module 160 displays a calculated tip position of the CVC relative to the target position and indicates if the tip of the CVC is correctly positioned or not. Adjust the position of the CVC as necessary. After the position has been reached, disconnect the adaptor 130 and remove the guidewire.

An exemplary method of confirming the position of a tip of an endovascular device, such as a central venous catheter (CVC) is presented below. Access the implanted, static CVC using the adaptor 130. Connect adaptor 130 to the ivECG signal acquisition module 140. Flush the lumen of the CVC with electro-conductive (saline) solution to create a conductive saline column between the adaptor 130 at a proximal end, and a distal tip of the CVC catheter. The adaptor 130 provides an electrical connection between the saline column and the ivECG signal acquisition module 140. The Multiscale Complexity Analysis Module 150 receives ECG signals from the ivECG signal acquisition module 140 and calculates a PxI parameter. The audio/visual/tactile notification module 160 displays a calculated tip position of the CVC relative to the target position and indicates if the tip of the CVC is correctly positioned or not. Adjust the position of the CVC as necessary. After the position has been reached, disconnect the adaptor 130.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A system for confirming a tip location of a catheter previously placed within a patient, the system comprising:
    an ivECG acquisition module;
    a multiscale complexity analysis module;
    a notification module, including one or more features selected from an audio feature, a video feature, and a tactile feature; and
    an adaptor configured to couple to the catheter previously placed within the patient, the adaptor configured to establish an electrical pathway with the ivECG acquisition module via a saline column or an electrically conductive device,
    wherein the multiscale complexity analysis module uses ivECG signals, provided by the ivECG acquisition module and the electrical pathway, to provide a PxI (proximity index), the notification module indicating a location of a distal tip of the catheter relative to a predetermined target location.

2. The system of claim 1, wherein the electrical pathway includes an embedded electrode extending from a proximal hub to the distal tip of the catheter.

3. The system of claim 1, wherein the electrically conductive device is configured to be disposed within a lumen of the catheter, extending from a proximal hub to the distal tip thereof.

4. The system of claim 3, wherein the electrically conductive device includes one of a stylet, a guidewire, and a trocar.

5. The system of claim 1, wherein the electrical pathway includes the saline column extending from a proximal hub to the distal tip of the catheter.

6. The system of claim 1, wherein the catheter is selected from the group consisting of a central venous catheter (CVC), a peripherally inserted central catheter (PICC), a hemodialysis catheter, a tunneled catheter, and a guiding catheter.

7. The system of claim 1, wherein the notification module includes the audio feature and the video feature.

8. The system of claim 1, wherein the notification module includes the tactile feature.

9. The system of claim 1, wherein the system further comprises one or more external electrodes to provide an external ECG.

* * * * *